US00PP19942P2

(12) United States Plant Patent
Sidhu

(10) Patent No.: US PP19,942 P2
(45) Date of Patent: Apr. 21, 2009

(54) ***SARCOCOCCA* PLANT NAMED 'SARSID 1'**

(50) Latin Name: *Sarcococca hookeriana var. humilis*
Varietal Denomination: Sarsid 1

(76) Inventor: Gurjit Sidhu, Sidhu & Sons Nursery Ltd., 9623 Sylvester Rd, Mission, BC (CA), V2V 7K6

( * ) Notice: Subject to any disclaimer, the term of this patent is extended or adjusted under 35 U.S.C. 154(b) by 0 days.

(21) Appl. No.: 12/075,529

(22) Filed: Mar. 12, 2008

(51) Int. Cl.
*A01H 5/00* (2006.01)

(52) U.S. Cl. ..... Plt./226
(58) Field of Classification Search ..... Plt./226
See application file for complete search history.

*Primary Examiner*—S. B McCormick Ewoldt
(74) *Attorney, Agent, or Firm*—Penny J. Aguirre

(57) ABSTRACT

A new cultivar of *Sarcococca* named 'Sarsid 1', characterized by its narrow, oblanceolate to elliptic shaped leaves, its dwarf, consistent, and dense but spreading plant habit that is suitable as a groundcover, its vigorous growth habit, and its small highly fragrant flowers that emerge in mid winter.

2 Drawing Sheets

RELATED APPLICATIONS

This application is co-pending with a U.S. Plant Patent application for a cultivar discovered from similar parentage entitled *Sarcococca* Plant Named 'Sarsid 2'. (U.S. co-pending application Ser. No. 12/075,490).

Botanical classification: *Sarcococca hookeriana* var. *humilis.*

Variety denomination: 'Sarsid 1'.

BACKGROUND OF THE INVENTION

The present invention relates to a new and distinct cultivar of *Sarcococca hookeriana* var. *humilis*. The new cultivar will be referred to hereafter by its cultivar name, 'Sarsid 1'. 'Sarsid 1' is an evergreen shrub grown for use as a landscape plant.

The inventor discovered 'Sarsid 1' as a naturally occurring whole plant mutation in spring of 2002 in his nursery in Mission, British Columbia, Canada. 'Sarsid 1' was selected as a single unique plant after evaluation of 2,000 seedlings derived from seed sown in 1999 of unnamed plants of *Sarcococca hookeriana* var. *humilis.*

Asexual reproduction of the new cultivar was first accomplished by the inventor using stem cuttings in winter of 2002 in Mission, British Columbia, Canada. The characteristics of this cultivar have been determined to be stable and are reproduced true to type in successive generations.

SUMMARY OF THE INVENTION

The following traits have been repeatedly observed and represent the characteristics of the new cultivar as grown outdoors in a trial garden for five years in Mission, British Columbia, Canada. These attributes in combination distinguish 'Sarsid 1' as a unique cultivar of *Sarcococca.*

1. 'Sarsid 1' exhibits narrow, oblanceolate to elliptic shaped leaves.
2. 'Sarsid 1' exhibits a dwarf, consistent and vigorous growth habit.

3. 'Sarsid 1' exhibits a consistent plant habit; forms a dense clump but slowly spreading by rhizomes; suitable as a groundcover.
4. 'Sarsid 1' produces racemes of small, nearly white, highly fragrant flowers in February in British Columbia, Canada.

'Sarsid 1' differs from its parent species *Sarcococca hookeriana* var. *humilis,* in having larger and narrower leaves and in having a more consistent plant habit and a more consistent and vigorous growth habit. 'Sarsid 1' can be compared to 'Sarsid 2', another selection of the inventor. 'Sarsid 2' is similar to 'Sarsid 1' in growth and plant habit, however 'Sarsid 2' has broader leaves. 'Sarsid 1' can be compared to *Sarcococca hookeriana* var. *digna* (not patented) as var. *digna* has similar narrow foliage, however, var. *digna* it is a much larger plant as 'Sarsid 1' is a cultivar derived from the dwarf var. *humilis.*

BRIEF DESCRIPTION OF THE DRAWING

The accompanying colored photographs illustrate the overall appearance and distinct characteristics of two year-old plants the new *Sarcocca* and comparison plants as grown in one-gallon containers in Mission, British Columbia, Canada.

The photograph in FIG. 1 provides a side view of 'Sarsid 1' in bloom.

Figure 1:
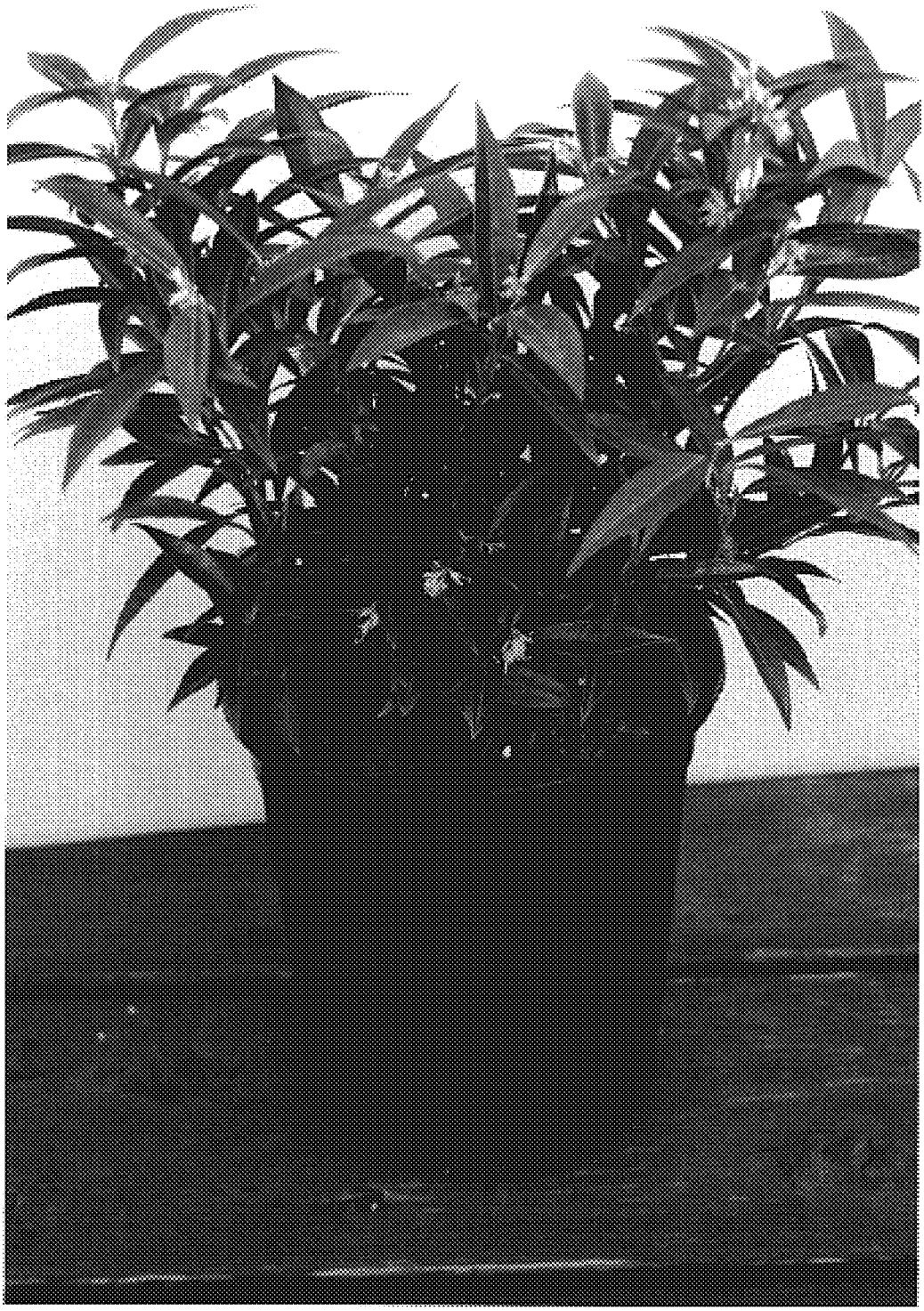
Figure 2:
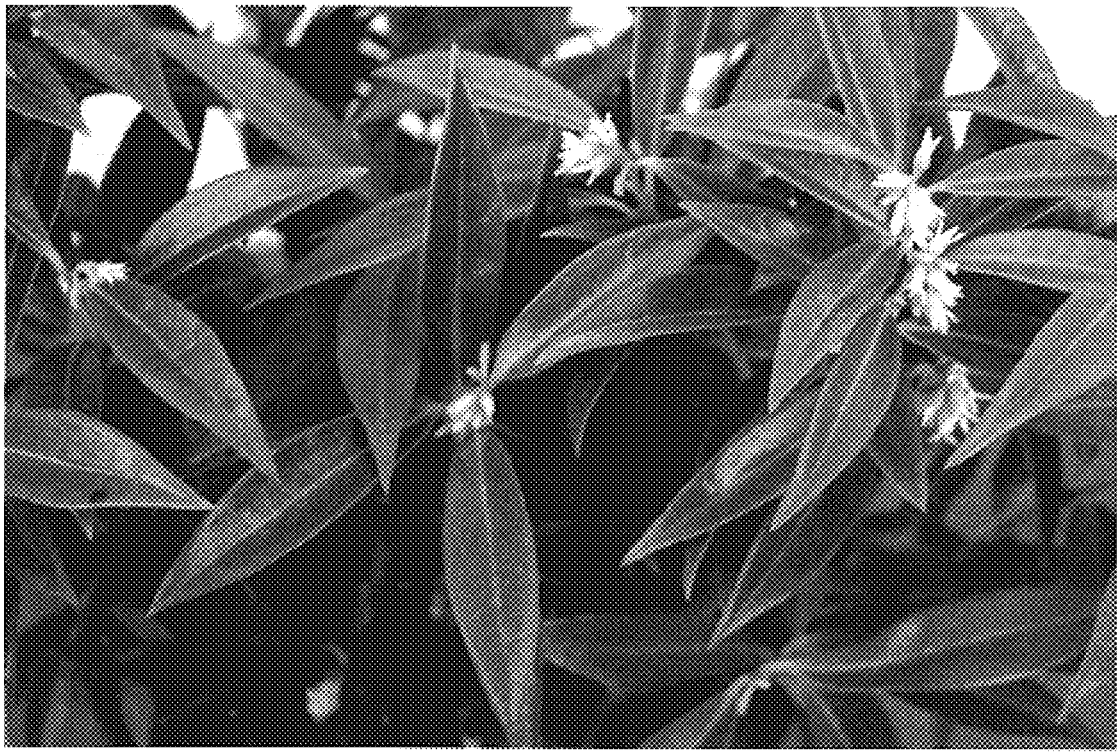

The photograph in FIG. 2 provides a close-up view of the foliage of 'Sarsid 1'.

Figure 3:
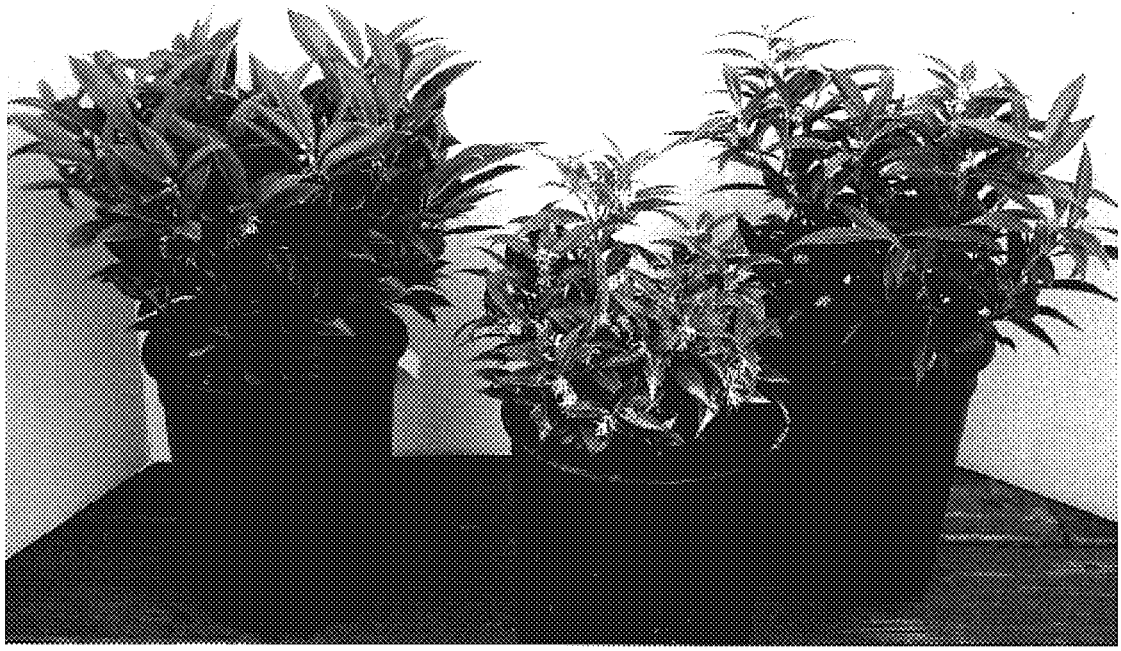

FIG. 3 provides a comparison of 'Sarsid 1' (right), *Sarcococca hookeriana* var. *humilis* (center), and 'Sarsid 2' (left).

The colors in the photographs are as close as possible with the digital photography techniques available, the color values cited in the detailed botanical description accurately describe the colors of the new *Sarcococca.*

DETAILED BOTANICAL DESCRIPTION

The following is a detailed description of two year-old plants of the new cultivar as grown outdoors in one-gallon containers in Mission, British Columbia, Canada. The phenotype of the new cultivar may vary with variations in environmental, climatic, and cultural conditions, as it has not been tested under all possible environmental conditions. The color determination is in accordance with the 2007 RHS Colour Chart of The Royal Horticultural Society, London, England, except where general color terms of ordinary dictionary significance are used.

General Description:

*Blooming period.*—Blooms for approximately 4 weeks beginning in early in February in Mission, British Columbia, Canada.

*Plant habit.*—Relatively dwarf, evergreen shrub with an upright, dense habit but slowly spreading habit.

*Height and spread.*—About 21 cm in height and 25 cm in width in a one gallon container, the original plant reached a height of about 70 cm in height and about 91 cm in width after seven years of growth.

*Cold hardiness.*—U.S.D.A. Zone 6.

*Diseases and pests.*—No susceptibility or resistance to diseases or pests has been observed.

*Root description.*—Fleshy from rhizomes 162D in color with an average width of 4 mm.

Growth and Propagation:

*Propagation.*—Stem cuttings.

*Root initiation.*—Roots develop in about 6 weeks in winter at 20° C.

*Time required for root development.*—About 2 years to finish a one gallon container from a cutting.

*Growth rate.*—Vigorous relative to parent species.

Stem Description:

*Shape.*—Oval.

*Stem color.*—New growth emerges N 144A, maturing to 137C.

*Stem size.*—Main stems; about 21 cm in length and 2 mm in diameter, lateral branches; about 6 cm in length and 2 mm in width.

*Branching.*—From 2 to 4 lateral branches.

Foliage Description:

*Leaf shape.*—Narrowly oblanceolate to narrowly elliptic.

*Leaf division.*—Simple.

*Leaf base.*—Cuneate.

*Leaf apex.*—Acuminate.

*Leaf fragrance.*—None.

*Leaf venation.*—Pinnate, only midrib is conspicuous, 144B in color on upper surface and 144D in color on lower surface.

*Leaf margins.*—Entire.

*Leaf arrangement.*—Primarily alternate with some opposite.

*Leaf attachment.*—Petiolate.

*Leaf surface.*—Glabrous and shiny on upper surface, glabrous and dull on lower surface, leathery.

*Leaf size.*—Average of 5.7 cm in length and 1.3 cm in width.

*Leaf quantity.*—Average of 25 leafs per stem 20 cm in length.

*Leaf color.*—Newly expanded leaves; upper surface 144A, lower surface 145A, mature leaves; upper surface N137A, lower surface 137C.

*Petioles.*—About 7 mm in length and 2 mm in width, glabrous surface, 145A in color.

*Stipules.*—None.

Inflorescence Description:

*Inflorescence type.*—Short racemes of small, apetalous, non-showy flowers emerging from leaf axils with male flowers near apex and female flowers near base of raceme.

*Flower fragrance.*—Highly scented, hyacinth-like.

*Lastingness of inflorescence.*—About 10 days.

*Flower quantity.*—Average of 3 racemes per lateral stem and 8 flowers per raceme.

*Flower type.*—Tubular, apetalous, reproductive organs surrounded by imbricate sepals.

*Flower size.*—Male; average of 3 mm in diameter and 5 mm in depth, female; average of 6 mm in length and 2 mm in width.

*Raceme size.*—About 1 cm (from base of peduncle) in length and about 5 mm in diameter.

*Peduncles.*—About 3 mm in length and 1 mm in diameter, 144B in color, surface glabrous.

*Pedicels.*—About 1 mm in length and width, 144B in color, surface glabrous.

*Flower buds.*—Oblong in shape, up to 5 mm in length and 2 mm diameter, color; blend of 144D and 155C with a blush of 73B.

*Petals.*—None.

*Sepals.*—Male flowers; 4, ovate in shape, imbricate and opening to a campanulate shaped calyx, color a blend of 144D with 155C with a blush of 73B, glabrous surface, about 4 mm in length and 2 mm in width, entire margin, round apex and attenuate base, female flowers; 4, un-fused but remain imbricate into tube about 4 mm in length and 2 mm in width, 144B in color, glabrous surface.

*Imbricate bracts.*—Male flowers, about 1 mm in length and width, 144B in color, female flowers; about 2 mm in length and width and surrounding pedicel, 144B in color, glabrous surface.

Reproductive Organs:

*Gynoecium.*—1 pistil, 2 stigmas that are recurved at tube apex and 144B in color at base and 144D in color at apex, about 2 mm in length and 0.5 mm in width, style and ovary is not discernable.

*Androcoecium.*—4 stamens, un-fused and exserted, filaments are 155A in color, about 5 mm in length and 1 mm in width, anthers are basifixed, about 1 mm in length and 0.7 mm in width and 182B in color, pollen is moderate to scarce in abundance and 198D in color.

*Fruit and seed.*—Berry production was not observed on the plants available for data collection, globose purplish-black drupe may form under the right conditions.

It is claimed:

1. A new and distinct cultivar of *Sarcococca* plant named 'Sarsid 1' as herein illustrated and described.

* * * * *